United States Patent [19]

Sundrehagen

[11] Patent Number: 5,352,616
[45] Date of Patent: Oct. 4, 1994

[54] ANALYTE VARIANT ANALYSIS

[75] Inventor: Erling Sundrehagen, Oslo, Norway

[73] Assignee: Axis Biochemicals AS, Oslo, Norway

[21] Appl. No.: 958,326

[22] PCT Filed: Jun. 20, 1991

[86] PCT No.: PCT/EP91/01145
§ 371 Date: Feb. 19, 1993
§ 102(e) Date: Feb. 19, 1993

[87] PCT Pub. No.: WO91/19993
PCT Pub. Date: Dec. 26, 1991

[30] Foreign Application Priority Data
Jun. 21, 1990 [GB] United Kingdom ............... 9013895
Jan. 30, 1991 [GB] United Kingdom ............... 9102024

[51] Int. Cl.$^5$ ............... G01N 33/53; G01N 33/564
[52] U.S. Cl. ............... 436/501; 436/514; 436/516; 436/541; 436/808; 435/7.1; 435/18; 435/775; 422/61
[58] Field of Search ............... 436/501, 541, 516; 435/18, 964, 7.1

[56] References Cited

U.S. PATENT DOCUMENTS 4,338,396 6/1982 Kiyasu .................. 435/17
4,626,355 12/1986 Joustra et al. ........... 436/161
5,215,892 6/1993 Kishimoto et al. ........ 435/69.1

FOREIGN PATENT DOCUMENTS

WO85/03578 8/1985 PCT Int'l Appl. .

OTHER PUBLICATIONS

Gosling, Clin. Chem. 36(8): 1408–1427, 1990.
Cavalli-Sforza et al., Am. J. Hum. Genet. 29:581–592, 1977.
Kawasaki et al., J. Chromitog., 226:1–12, 1981.
Schellenberg et al., Alcoholism: Clinical Exp. Res., 13(5): 605–610.
Pekelharing et al., Anal. Bioch. 165:320–326, 1987.
Edwards, Biochem. J., 200, 1–10 (1981).
Kenney, J. Chem. Tech. Biotechnol., 39, 173–182 (1987).
Storey et al., Clin. Chem., 31(9), 1543–1545 (1985).
Vesterberg et al., Clinica Chimica Acta., 141, 33–39 (1984).

Primary Examiner—Christine M. Nucker
Assistant Examiner—Chris Dubrule
Attorney, Agent, or Firm—Bacon & Thomas

[57] ABSTRACT

The present invention provides a method of assessment of the concentration of a subset of variants in a population of proteinaceous analyte variants capable of separation by a fractionation system, wherein said population of variants are contacted with a population of labelled proteinaceous specific binding partners therefor to form labelled binding partner-analyte complexes therewith, which are then subjected to separation by the said fractionation system into one or more fractions containing said subset of analyte variants in complexed form and assessment of the amount of label in one or more fractions so obtained, the said population of specific binding partners having, prior to reaction, substantially uniform distribution or mobility in said fractionation system, compositions and test kits for use in such methods. The method of the invention is particularly suitable for the analysis of variants of the protein transferrin.

15 Claims, 9 Drawing Sheets

ANALYTE VARIANT ANALYSIS

The present invention relates to a method of assessing the concentration of a subset of analyte variants within a group of different analyte variants, and to test kits and reagent compositions for use in such a method.

Biological molecules such as enzymes, antigens and other biologically important proteins frequently occur as a population of variants which, although sharing a common biological function or property e.g. antigenicity or enzymic activity, differ slightly in their structure. This variance in structure may be due to differences in primary, secondary or tertiary structures in the amino acid sequences of proteins or polypeptides or to differences in the carbohydrate moieties or the lipid composition of the molecule. Although a common characterising property or function between the variant molecules in a given population is retained, such differences in their structure often serves to alter other properties of the variants for example size, charge, isoelectric point (pI) which in turn alters their behaviour in different fractionation and separation systems and may be used as the basis for separating one or more such variants in a variant mixture.

Enzymes frequently occur as variants e.g. isoenzymes and many other biological proteins are now known to exist in two or more variant forms, frequently differing in the extent of glycosylation of the protein or in the carbohydrate composition. The relative concentrations of such variants in a given body tissue or fluid are generally constant but may be disturbed in certain diseases or pathological states or as a result of other disturbances to the body. Thus, for example the ratio of glycosylated to non-glycosylated haemoglobins is known to increase in the serum of patients suffering from diabetes. Similarly certain structural proteins of analytical interest e.g. myoglobins may have slight structural differences in different organs and may be released into the bloodstream following cell damage resulting from disease or injury.

Thus, by measuring the levels of the different variants in the blood or other body tissue or fluid a diagnosis or assessment of the state of a disease or cellular damage can be made.

Of particular importance in this regard is the assessment of the levels of different variants of the protein transferrin in the serum. Transferrin generally occurs in sialylated forms i.e. carrying three or more sialyl residues. However in chronic alcohol abusers, desialylated transferrin i.e. transferrin carrying two or less sialyl residues, is relatively increased in content compared to non-alcoholics e.g. from a normal level of about 1-3% to about 6-25% of the total transferrin content of the patient's serum. Desialylated transferrin, often termed carbohydrate deficient transferrin (CDT), is now generally regarded as a clinically reliable marker for chronic alcoholism. However present methods of transferrin variant quantitation are time consuming and require advanced biochemical equipment. Thus, in the absence of a simple and convenient test for the desialylated transferrin marker, chronic alcohol abuse is still presently diagnosed on the basis of clinical history, information from the patients themselves regarding their alcohol consumption, and a number of laboratory tests, all of which have limited sensitivity and specificity. Blood alcohol level is a reliable measure only when block is sampled within 24 hours after alcohol consumption. All present clinical chemistry tests have sensitivities and specificities too low to reliably identify all alcohol The microheterogeneity of transferrin and its correlation with alcohol abuse were first detected in 1980. (Stibler H, Sydow O, Borg S. "Quantitative estimation of abnormal microheterogeneity of serum transferrin in alcoholics". Pharmac. Biochem. Behav, 1980, 13 Suppl. 1,47–51). The clinical importance of this microheterogeneity has been further investigated, and isoelectric focusing and chromatofocusing methods for the quantitative separation of the different transferrin variants have been studied (Vesterberg O, Petren S. and Schmidt E.:"Increased concentrations of a transferrin variant after alcohol abuse". Clinical Chemica Acta, 141 33–39, 1984. Storey E.L., Mack U., Powell L.W. and Halliday J.W.:"Use of chromatofocusing to detect a transferrin variant in serum of alcoholic subjects". Clin. Chem. 31: 1543–1545, 1985). Joustra and Blanche filed in 1984 a method patent application in Sweden and Stibler, Borg and Joustra published in 1984 a mini column anion exchange chromatography method for quanti-filtration of carbohydrate-deficient transferrin in serum in relation to alcohol consumption. (Stibler H. Borg S. and Joustra M.: Alcoholism 10: 535–544, 1986. Joustra M. & Blanche C. Swedish patent application 8400587-5). These methods are based on isocratic ion exchange chromatography separation of the transferrin variants fractions in serum samples, followed by double antibody radioimmunoassay quantitation of the transferrin content of the different fractions. This ion exchange chromatography technique separates all transferrin components having 2 or less sialic acid residues which are thus isoelectrically above pH 5.65. Using this method 77 alcoholic patients could be clearly separated from 80 healthy "normal consumers" and total abstainers by having elevated transferrin variants with isoelectric points (pI) above pH 5.65.

The main difficulty with these methods is that they are cumbersome and time-consuming to perform. A two-step procedure is necessary requiring a chromatographic separation of the transferrin variants in the serum samples, followed by an immuneassay quantification of the transferrin variants thus separated.

A need therefore exists for a reliable and simple assay for different analyte variants within a mixed population of analyte variants, and in particular for an improved method of detecting the different variants of transferrin.

Such analyte variants of clinical interest are normally proteinaceous in nature and frequently have an easily identifiable proteinaceous binding partner with which they form a complex. Most commonly the analyte variant is antigenic and the binding partner is therefore an antibody, although many proteins are specifically known to bind other proteins or peptides and may thus be regarded as binding partners. Thus for example the protein haptoglobin is a specific binding partner for haemoglobin. Such binding partners can be labelled, e.g. with an enzyme or other reporter atom or group and can then be used in assay procedures to label the analyte variants of interest.

The present invention is based on the concept that proteinaceous analyte variants can be labelled prior to separation using labelled binding partners so that after separation assessment of the label in the separated fractions provides a quantitative indication of the relative abundances of the variants. However, it has been found important that the analyte variants are reacted with a population of labelled binding partners which are reactive to all the different analyte variants to be analysed but have a substantially uniform distribution or mobility in a chosen fractionation or separation system.

Such a procedure is substantially simpler in operation than prior systems using separation followed by conventional immunoassays on the separate fractions.

Thus in one aspect, the present invention provides a method of assessment of the concentration of a subset of variants in a population of proteinaceous analyte variants capable of separation by a fractionation system, wherein said population of variants is contacted with a population of labelled proteinaceous specific binding partners therefor to form labelled binding partner-analyte complexes therewith, which are then subjected to separation by the said fractionation system into one or more fractions containing said subset of analyte variants in complexed form and assessment of the amount of label in one or more fractions so obtained, the said population of specific binding partners having, prior to reaction, substantially uniform distribution or mobility in said fractionation system.

As used herein, the term "proteinaceous" is intended to include all molecules which are basically protein in nature, including both peptides and polypeptides, but which may carry additional moieties of a non-protein nature e.g. lipid or carbohydrate groups.

Since the binding partner in the variant/binding partner complex exhibits a substantially uniform distribution or mobility in the chosen fractionation system, the differences between the mobilities or distributions of the variant/binding partner complexes are due to the differences between the variants in those complexes, in other words, to the analyte variance. One or more fractions of these variant/binding partner complexes thus obtained may be separated by the chosen fractionation system and the amount of label in each separated fraction assessed.

In a further aspect the invention also provides a composition for performing the method of the invention comprising labelled proteinaceous binding partners e.g. antibodies or immunoreactive fragments thereof, which have a substantially uniform mobility or distribution in one or more fractionation In a yet further aspect there is provided an analytical test kit comprising said composition together with the reagents and/or materials required to perform the said fractionation.

Conveniently the analyte variants differ according to their charge in a given buffer system and thus may easily be separated by a charge-based system such as ion exchange chromatography or electrophoresis. Alternatively the analyte variants may differ in their isoelectric points (pI) and may be separated by isoelectric- or chromato-focusing. Thus for example the "Mono-P" column and "Polybuffer" chromatofocusing system of Pharmacia, Sweden may be used. Isoelectric focusing of the complexes can take place in two-dimensional gel sheets, or alternatively the complexes may be separated by simple electrophoresis in agarose gel. A wide range of ion exchange media and solid phases may be used in the method provided by this invention. The ionizable chemical residues on these media can be constituted by, but are not limited to, amine residues or sulphonated or carboxylated residues, and may be supported on beads, particles, gels, membranes, filters or any other suitable solid phase. Although such fractionation systems are simple to use and give good results and are thus preferred according to the invention, any other fractionation system utilising a property in which the analyte is variant and in which the chosen binding partner therefor is constant, may be used.

Resins or particles may be used in slurry batch forms or in columns. Columns may be eluted with salt or pH gradients or by isocratic elution. From a practical point of view, slurry batch forms and isocratic elution are preferred. Magnetizable particles were found to be especially advantageous. The ion exchange solid phase may also be constituted by a rigid three dimensional structures or by ion exchange filters. If a filter is used, the filtration may be performed parallel to the surface, e.g. radially or along a filter strip.

Conveniently all or some of the various reagents and components required to perform the separation step are supplied in kit form together with the labelled binding partner composition. As mentioned above this forms a further aspect of the invention.

Such reagents and materials generally include buffer salts or solutions, surfactants e.g. Tween® and such like, preservatives e.g. sodium azide, the various gels, resins or other media required to perform the fractionation step, optionally ready assembled for use e.g. as columns etc.

As previously indicated, subsequent to the formation of the analyte variant/binding partner complexes, the complexes are isolated and the amount of label present in the complex fraction(s) is assessed.

Such labels may be constituted by any conventional labelling system known in the art. Thus, the labels may be fluorescent, coloured, radioactive or enzymic and may be assessed by known means. Radioactive labels would generally be chosen from radioisotopes conventionally used in radioimmunoassay e.g. $I^{125}$, and many fluorescent or coloured labels have been described. Thus suitable fluorescent labels include dimethylaminonaphthalene, fluorescein, dichlorotriazinylaminofluorescein or fluorescent metal compounds. Examples of coloured labels include 4-dimethylaminobenzene, 4-N,N-dimethylaminoazobenzene, trinitrobenzene, benzofurazines, tetramethylrhodamine, texas red, morpholinorhodamine and derivatives thereof, azobenzenes, anthraquinones, oxazines, thiazines, triazines, porphyrins, phycobilins, chorophylls, indigo dyes and analogs or derivatives thereof.

As mentioned above any proteinaceous binding partner for the analyte in question may be used provided that it has uniform mobility or distribution in the chosen fractionation systems. Antibodies are generally preferred binding partners for antigens and haptens but other binding partner systems maybe employed to suit the situation e.g. haptoglobin-haemoglobin or hormone-receptor systems.

Immunoreactive antibody fragments e.g. F(ab) or F(ab')$_2$ fragments may also be used as long as the behaviour of the fragment in the given fractionation system remains uniform. Such fragments may usefully be S-blocked, for example with S-carboxymethyl groups.

F(v) fragments, that is the hypervariable regions of F(ab) fragments may also be used and may be of synthetic origin, via recombinant DNA technology or chemical synthesis.

We have found that where the molar amount of a labelled antibody or F(ab)$_2$ fragment is approximately equal to or in excess of that of the analyte, significant cross-linking occurs due to the divalent reactivity of the labelled reagent. This gives a low estimate of the number of analyte molecules. In many cases, therefore, it is preferred to use monovalent labelled analyte-binding partners, especially F(ab) or F(v) fragments of appropriate antibodies.

It should be noted that such monovalent fragments are likely to be subject to less variability, especially when produced synthetically, and if carefully labelled in a uniform manner, may not require a fractionation step in order to achieve the criterion of uniform mobility or distribution in the chosen fractionation system.

Hereinafter, for simplicity, references to 'antibodies' include fragments of antibodies unless stated otherwise.

The method of the invention is particularly suited to the analysis of levels of different variants of transferrin. Thus in a special embodiment this invention provides a method for the assessment of variants of transferrin often named isotransferrins, in blood plasma, serum, whole blood or hemolysate. As previously mentioned, the transferrin variants differ mainly in the different numbers of sialic acid residues on the transferrin molecules. The new method of the invention preferably comprises contacting the sample with a population of labelled antibodies reactive to human transferrin and having a substantially uniform mobility or distribution in an fractionation system selected from electrophoresis, ion exchange, chromatofocusing or isoelectrofocusing. Preferably the antibody binding step takes place in a ferric ion-containing buffer solution allowing antigen-antibody complexes to be formed. Such antigen-antibody reactions favourably take place close to neutral pH, preferably between pH 5 and pH 9, and at a salt concentration and composition not prohibiting such antigen-antibody complexes to be formed.

The labelled antibodies are preferably monoclonal antibodies but polyclonal antibodies may be used since the purification treatments described herein ensure uniform properties.

Labelled F(ab) or F(v) fragments of anti-transferrin antibodies are novel substances of especial use in transferrin variant analysis. Even when relatively non-uniform, they are capable of giving better results than whole antibodies. Fractionated labelled F(ab) and F(v) fragments which are of uniform mobility or composition in one or more fractionation systems are particularly preferred.

The transferrins of the sample may be saturated with ferric ions prior to or simultaneously with or subsequently to the exposure to the antibodies. Ferric ion saturation of the transferrins prior to or simultaneously with the separation of the antigenanti-body complexes by means of the said separation systems is generally necessary for transferrin variant analysis by this technology, since differences in the ferrous ion content of the variants will erase the distribution pattern in the said separation systems obtained due to the differences in sialic acid content.

The preferred method of the invention for transferrin variant analysis requires subjecting the mixture of variant/antibody complexes to a chromatofocusing, ion exchange, electrophoresis or isoelectric focusing separation system. Since the labelled antibodies have a substantially uniform mobility or distribution in one of these separation systems, these labelled antibodies form antigen-antibody complexes with the transferrin variants (isotransferrins) with differences in mobility or distribution in one of the said separation systems corresponding to but not necessarily identical to, the mobility or distribution differences between the transferrin variants. Monoclonal antibodies reactive to human transferrin in general and having a substantially uniform mobility or distribution in one of the said separation systems may be produced by conventional hybridoma techniques, and can be modified by chemical techniques if necessary. Purification of the desired antibodies is generally required and is preferably achieved using one of the said systems e.g. by chromatofocusing, ion exchange chromatography, isoelectric focusing or electrophoresis.

A test kit according to the invention for use in transferrin analysis preferably comprises labelled anti-transferrin antibodies, or especially preferably labelled Fab fragments of such antibodies, together with at least one ferric ion salt or solution.

In several embodiments of the method of this invention, labelled antibodies or other proteinaceous binding partners with selected ranges of isoelectric points or exhibiting a special distribution or mobility in the said separation systems are preferred. To obtain such modified proteins, the proteins may be modified prior to or after the labelling step. In general, such modifications will alter the number of charged groups, e.g. acidic or basic groups, in the molecule. Such modification can be achieved by the use of reagents reacting with the side chains of the amino acids of the proteins, as described for example in Glazer, Delange and Sigman: "Chemical modification of proteins", Elsevier Biomedical Press, Amsterdam, New York, Oxford 1975, and other relevant literature. As an example, amine residues can be modified by carbamylation, acetylation, benzylation or succinylation, and carboxylic acid residues can be modified by esterification and coupling to nucleophiles by the use of carbodiimides or other coupling agents. Similarly, the carbohydrate moieties of antibodies or other proteinaceous binding partners can be modified.

A convenient method for the modifications often necessary for the preparation of the labelled glycoprotein binding partner compositions of this invention is the periodate oxidation of the carbohydrate moieties of glycoproteins followed by reaction of the resulting aldehyde with reagents introducing acidic or basic groups. Another convenient method appropriate to proteins having disulphide bridges is the partial reduction of the disulphide bridges of cystine between the amino acid polypeptide chains of the proteins. Antibodies in particular contain several such disulphide linkages, and several, but not all, of the disulphide linkages can be reduced to free thiols Without compromising the affinity of the antibodies for the antigens. These linkages, and thus the resulting thiols, are located in the hinge region of the antibodies, remote from the antigen-binding sites of the antibodies. 2-thioethanol and dithiothreitol are examples of such reducing agents, but not in a limiting sense. Following removal of the reducing agent, reagents introducing acidic or basic groups are linked to the free thiols, by means of bifunctional coupling agents reacting with thiol moieties and nucleophilic moieties, e.g. sulfosuccinimidyl-4-(N-maleimidomethyl) cyclohexane-1-carboxylate, sulfosuccinimidyl(4-iodoacetyl) aminobenzoate or other succinimidylmaleimide containing reagents, in a single or a two step procedure. Alternatively, the reagent introducing acidic or basic groups may be linked by means of substituted pyridyl disulfides or thiol-containing reagents reestablishing a disulfide linkage, but carrying a chemical moiety of acid or basic chemical properties.

In a special embodiment of the invention, the nucleophilic reagent can be constituted by an acid polymer, e.g. polypeptides with one or more acidic side chains on the amino acids.

The advantage of carbohydrate modification and/or modification by reduction of cystine in the hinge region is the minor interference with the antigen binding sites of the antibodies thus obtained. However, acidic polypeptides may also be linked to lysine residues or other residues of the polypeptide structure of the antibodies.

In the case of transferrin variant analysis transferrin variants carrying two or less sialic acid residues and having a pI value higher than the transferrin variants with three or more sialic acid residues, are of special interest. An embodiment of this invention uses anion exchange resins at a pH and buffering salt concentration and composition where the antigen-antibody complexes of transferrin variants with three or more sialic acid residues bind to the anion exchange solid phase, as opposed to the antigen-antibody complexes with transferrin variants having 2 or less sialic acid residues, which do not. In this embodiment, labelled antibodies, modified if necessary, which bind to the anion exchange solid phase are preferred, thus leaving only in solution only the labelled antibody which has formed complexes with transferrin variants having 2 or less sialic acid residues. This is illustrated schematically in FIG. 1. The actual separation pH and buffer composition is chosen based upon the pI of the labelled monoclonal antibodies and complexes formed. After separation e.g. by centrifugation or filtration if the solid phase is in slurry batch form, or by magnetic separation if the solid anion exchange phase is magnetizable or by elution if the solid phase is in a rigid or a column form, measurements of the label remaining in the solution are used to obtain an assessment of the concentration of the antigen-antibody complexes, which correspond to the concentration of the transferrin variants having two or less sialic acid residues.

The method of this invention may be performed with labelled binding partners at a concentration in excess of the total amount of analyte (all variants) or with the analyte in excess of the binding partners. When binding partners are used in excess, signals corresponding to the total concentration of the different variants are obtained. When analyte is present in excess, signals corresponding to the relative amount of the different variants relative to the total concentration of all variants are obtained.

Where the labelled binding partner is to be used in excess, it is preferably monovalent. As indicated above, divalent binding partners such as antibodies tend to cross-link to two separate analyte molecules especially when used in approximately equimolar quantities. Thus, for this purpose, F(ab) or F(v) fragments are preferred.

In the case of a binding partner system using antibodies or fragments thereof against antigen analytes, if an antigen excess is used, labelled antibodies, modified if necessary, purified by means of affinity chromatography using immobilized antigens can optionally be used. Thus close to 100% of the antibodies or fragments can be immunoreactive, thus reducing the fraction of free non-complexed antibodies or fragments in the assay to a very low level. In this way potential interference in the antigen variant analysis method can be reduced or avoided.

The advantage of this invention is the combination of immunological quantitation and fractionation in one operation obtained by separating the complexes formed between the labelled binding partners and the different analyte variants followed by immunological quantitation. Thus this invention makes it possible to measure transferrins and other analyte variants far more easily than in the prior art, particularly for the purpose of measuring transferrin variants with low sialic acid content in blood serum of plasma from persons undergoing investigations related to alcohol consumption.

The following Examples are provided to illustrate the invention in a non-limiting manner, with reference to the drawings in which.

Figure 6:
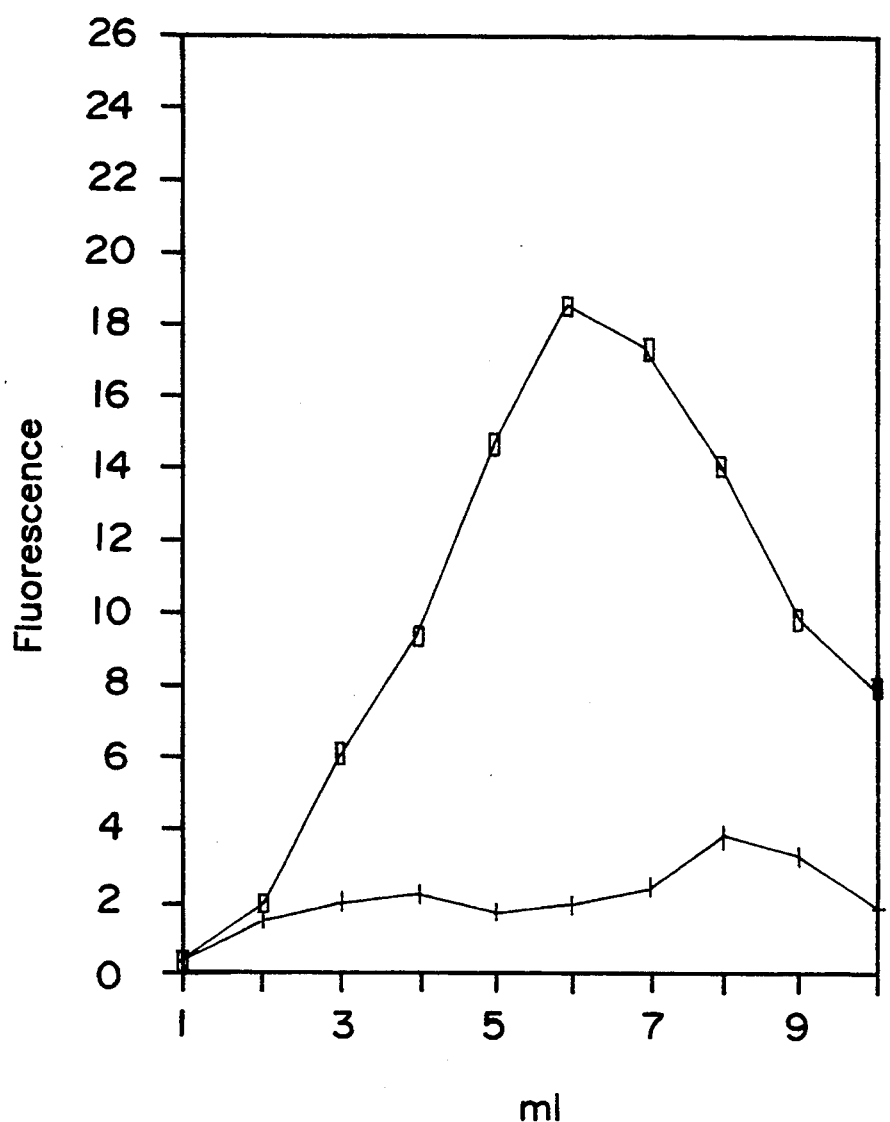
Figure 7:
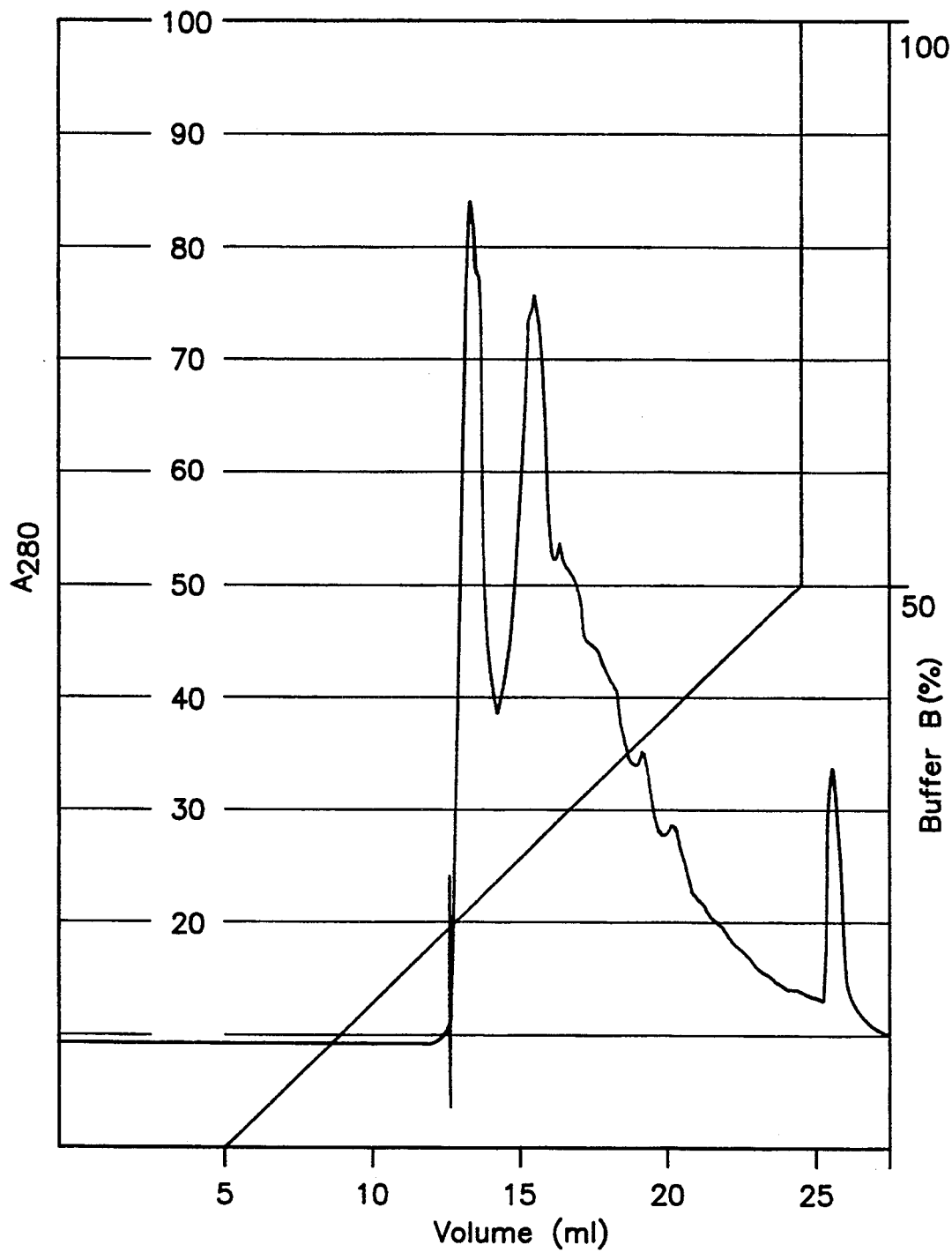
Figure 8:
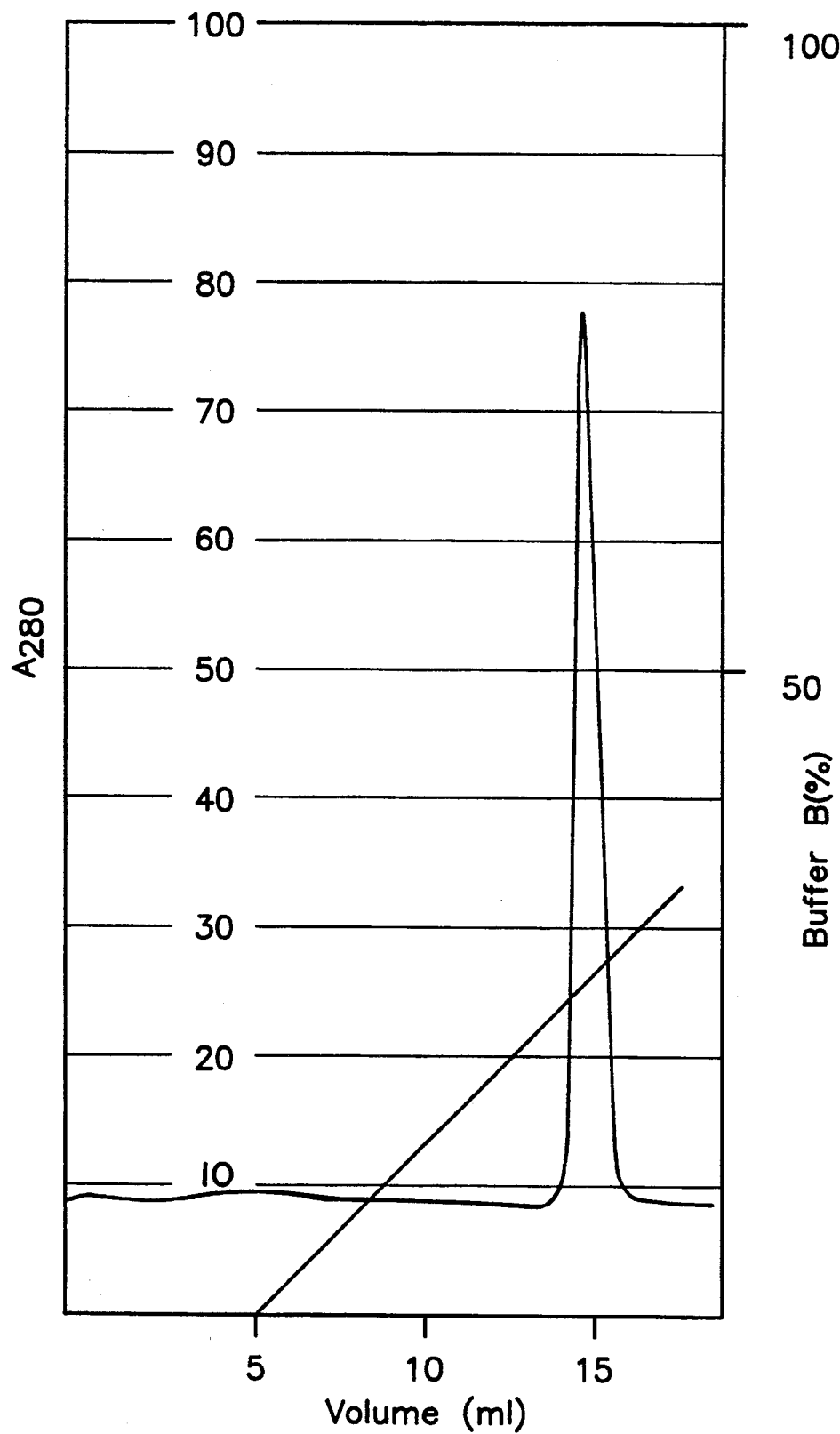
Figure 9:
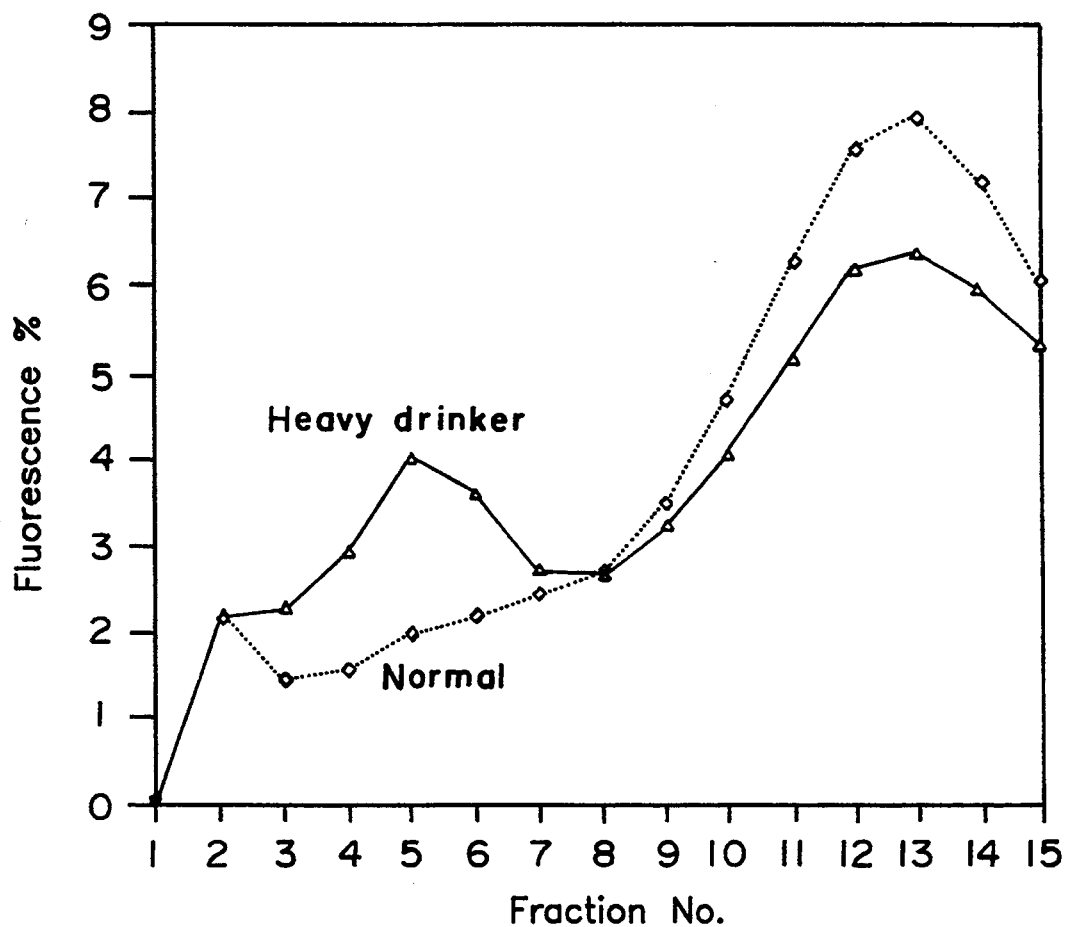

FIG. 6 shown graphically the fluorescence signals of fractions obtained from ion-exchange chromatography of complexes of anti-transferrin monoclonal antibodies and disialo- (□) and tetrasialo- (+) human transferrin;

FIG. 7 shows graphically the results of preparative anion exchange chromatography of a labelled non-purified preparation of monoclonal anti-transferrin antibodies;

FIG. 8 shows graphically the mobility in an anion exchange system of a single fraction obtained from the chromatography of FIG. 7;

FIG. 9 shows graphically the fluorescence of fractions of FITC-Fab-transferrin complexes from serum samples from a heavy drinker (-Δ-) and a normal subject (...O...) eluted from an anion exchange (mono Q) column.

EXAMPLE 1

Figure 1:
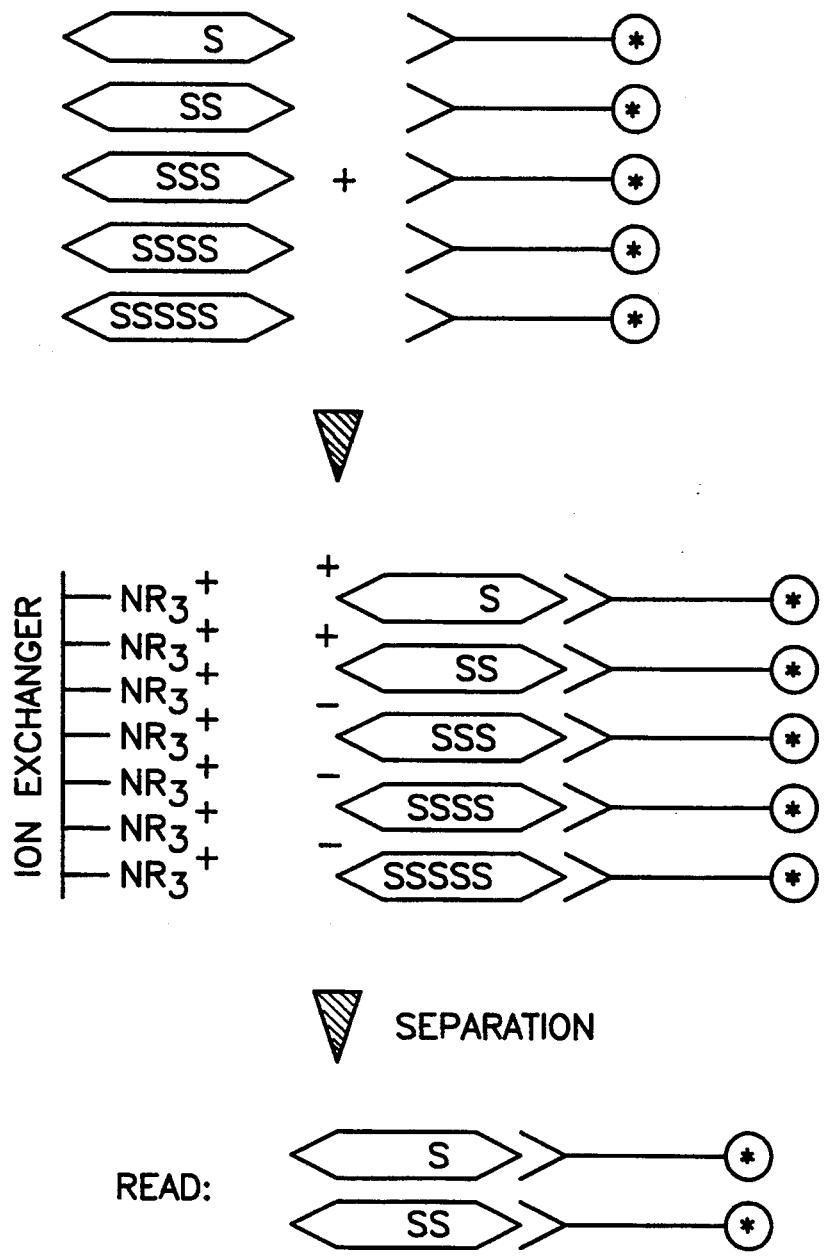
FIG. 1 is a schematic representation of the performance of the method of the invention for the assessment of variants of transferrin differing in the number of sialic acid residues.
Figure 1:
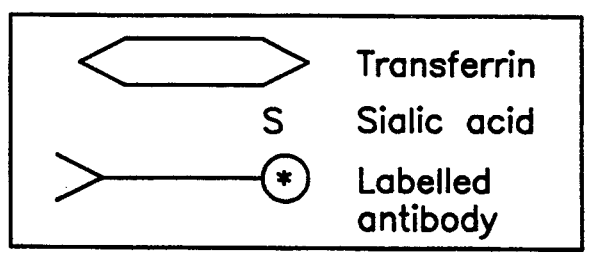
Figure 2:
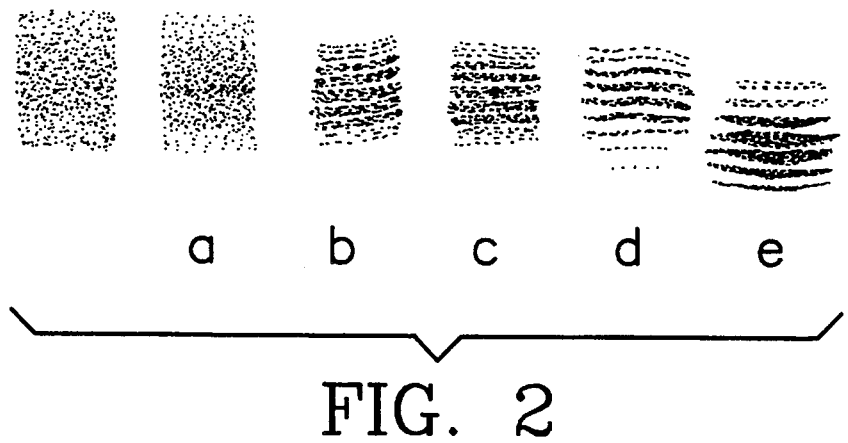
FIG. 2 represents an isoelectric focussing gel showing the pI of modified and labelled antibodies against human transferrin.

From commercially available ascites produced in mice with a anti-transferrin IgG-producing hybridoma, monoclonal antibodies were purified by means of ion exchange chromatography and gel chromatography in phosphate buffer. The immunoaffinity of the antibodies was assayed by a microtitre ELISA system using immobilized human transferrin and peroxidase-conjugated polyclonal anti-mouse-IgG antibodies in solution. The purified antitransferrin antibodies were dialysed against 0.1 M acetic acid buffer of pH 5.6, and oxidized by periodate ions (50 mM final concentration). After the removal of the periodate ions by gel chromatography, the antibodies were reacted with the acid polypeptide N-ala-ala-ala-ala-glu-glu-glu-glu-glu-COOH in 50 times molar excess to the antibodies followed by a stabilization of the binding by means of cyanoborohydride ions in solution (final concentration = 15 mM). The resulting modified antibodies were dialysed against 0.1 M sodium carbonate buffer pH 9.5, and reacted with 2-thioethanol at a final concentration of 10 mM for 30 minutes at room temperature, followed by removal of the 2-thioethanol by gel chromatography in phosphate buffer at pH 7.4. N-ala-ala-ala-ala-glu-glu-glu-glu-glu-COOH was reacted with the resulting free thiols of the protein by means of sulfosuccinimidyl-4- (N-maleimidomethyl)cyclohexane-1-carboxylate, with molar ratios of 1:33:40 of antibody: coupling reagent: peptide. After subsequent dialysis against carbonate buffer, the modified antibodies were reacted with fluorescein isothiocyanate, and subsequently purified by gel chromatography. At each step of these modifications, the antigen affinity was assayed, and only a very slight reduction was experienced. FIG. 2 shows the results of isoelectric focusing performed in gel electrophoresis (Phast System, Pharmacia), and exhibits the reduction in pI achieved. A substantial fraction of modified and labelled antibodies have a pI similar to or lower than the isotransferrins with two or less sialic acid residues. In this Figure (a) to (e) indicate as follows:

a) Human transferrin
b) Unmodified monoclonal antitransferrin IgG
c) Same as b), but where ala-ala-ala-ala-glu-glu-glu-glu-glu-has been coupled to the carbohydrate moieties.
d) Same as c), but where in addition ala-ala-ala-ala-glu-glu-glu-glu-glu has been coupled to the hinge region.
e) Same as d), but where fluorescein isothiocyanate has been reacted with the protein.

For the performance of the method of the present invention, a substantially uniform distribution or mobility of the antibodies in the relevant separation system is necessary. If not, the heterogeneity of the antibody complexes will make the separation and quantitation of the complexes of the antibodies with the different antigen variants impossible.

Figure 3:
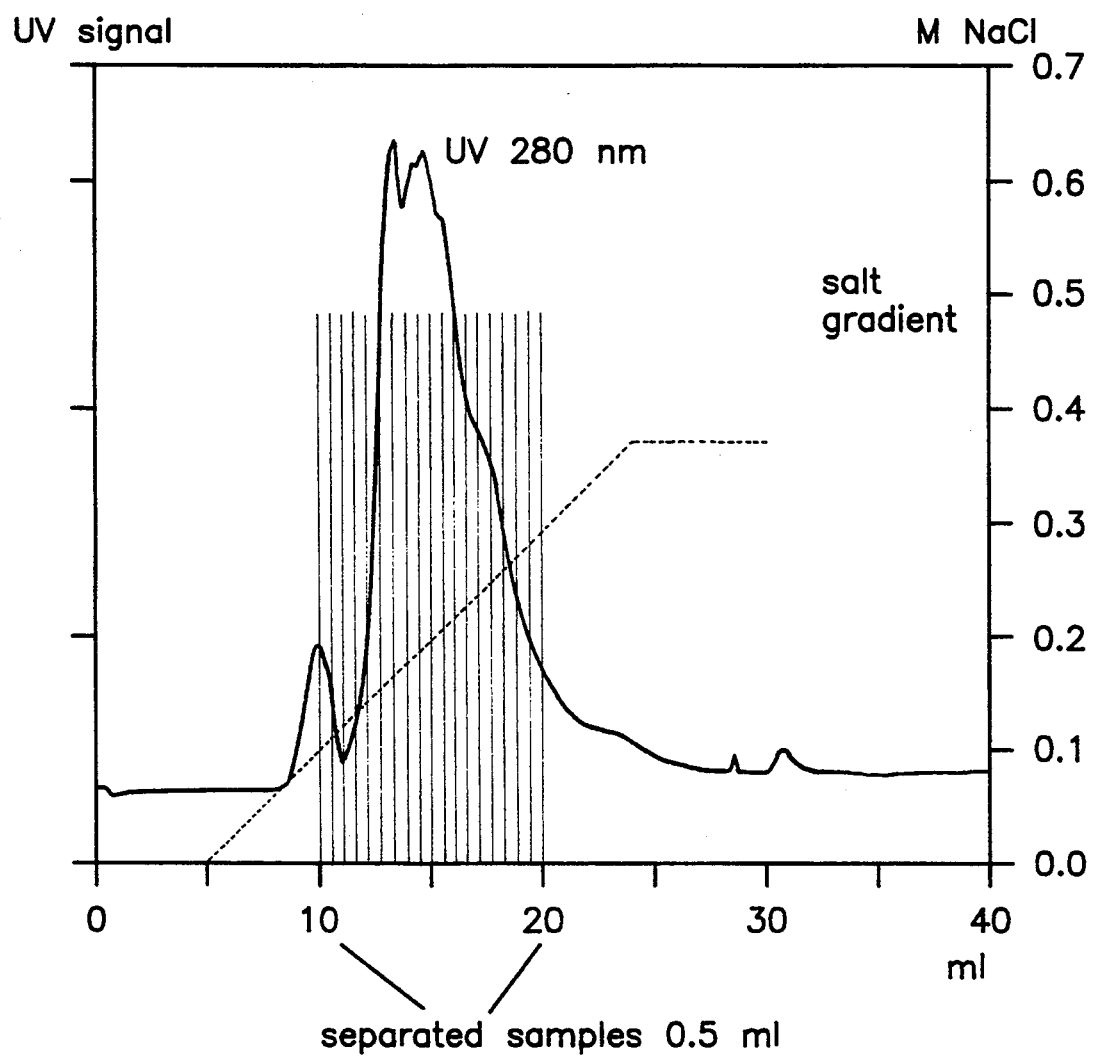
FIG. 3 shows graphically the separation of anti-transferrin FITC-derivatives by ion exchange chromatography on a strong anion exchange column (Buffer: 20 mM sodium phosphate pH 6.5). The solid line indicates UV Absorbance at 280 nm, the dotted line the salt gradient (M NaCl)

FIG. 3 demonstrates the heterogeneity of modified monoclonal antibodies evaluated by preparative anion exchange chromatography. The dotted vertical bars indicate the collection of 20 fractions from this preparative anion exchange chromatography, to obtain fractions with a narrow pH range.

Figure 4:
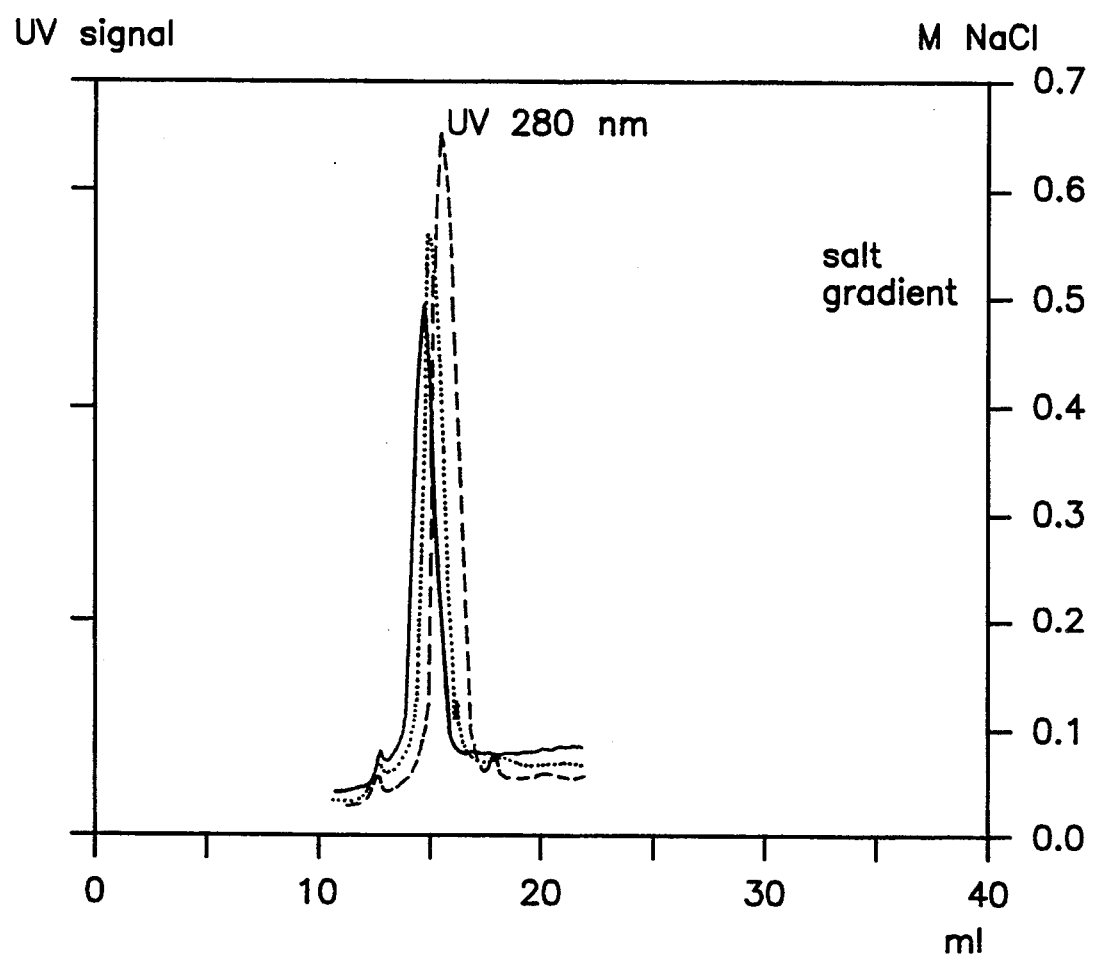
FIG. 4 shows graphically the further separation by re-chromatography on a strong anion exchange column, of 3 neighboring fractions of anti-transferrin FITC derivatives obtained from the preparation shown FIG. 2. (Buffer: 20 mM sodium phosphate pH 6.5)

FIG. 4 shows the results from an analytical chromatography of aliquots from three of the different neighboring fractions obtained from the said preparative chromatography, demonstrating that close to uniform mobilities were obtained for each fraction. Even more uniform fractions can be obtained by the use of a less steep gradient profile in the elution, repetitive chromatographies or other chromatographic techniques. Alternatively or in combination, preparative isoelectric focusing or chromatofocusing may be used.

When the test sample is mixed with the said labelled monoclonal anti-human-transferrin antibodies having a uniform or close to uniform mobility or distribution, antigen-antibody complexes with different mobilities or distribution in the corresponding separation system are formed reflecting the differences between the transferrin variants. The different antigen-antibody complexes are separated by ion exchange chromatography, chromatofocusing or isoelectric focusing or electrophoresis or other chemical techniques utilizing the differences in electric charge of the complexes formed.

EXAMPLE 2

Analysis of samples of sera from alcohol abusers and non-drinkers

Solid phase:
A 1 ml column of polystyrene particles with quaternary amine, substituted surface residues (Mono-Q column from Pharmacia, Uppsala, Sweden).

Eluent:
20mM bis-tris buffer with 100 mM sodium chloride, pH 6.50.

Figure 5:
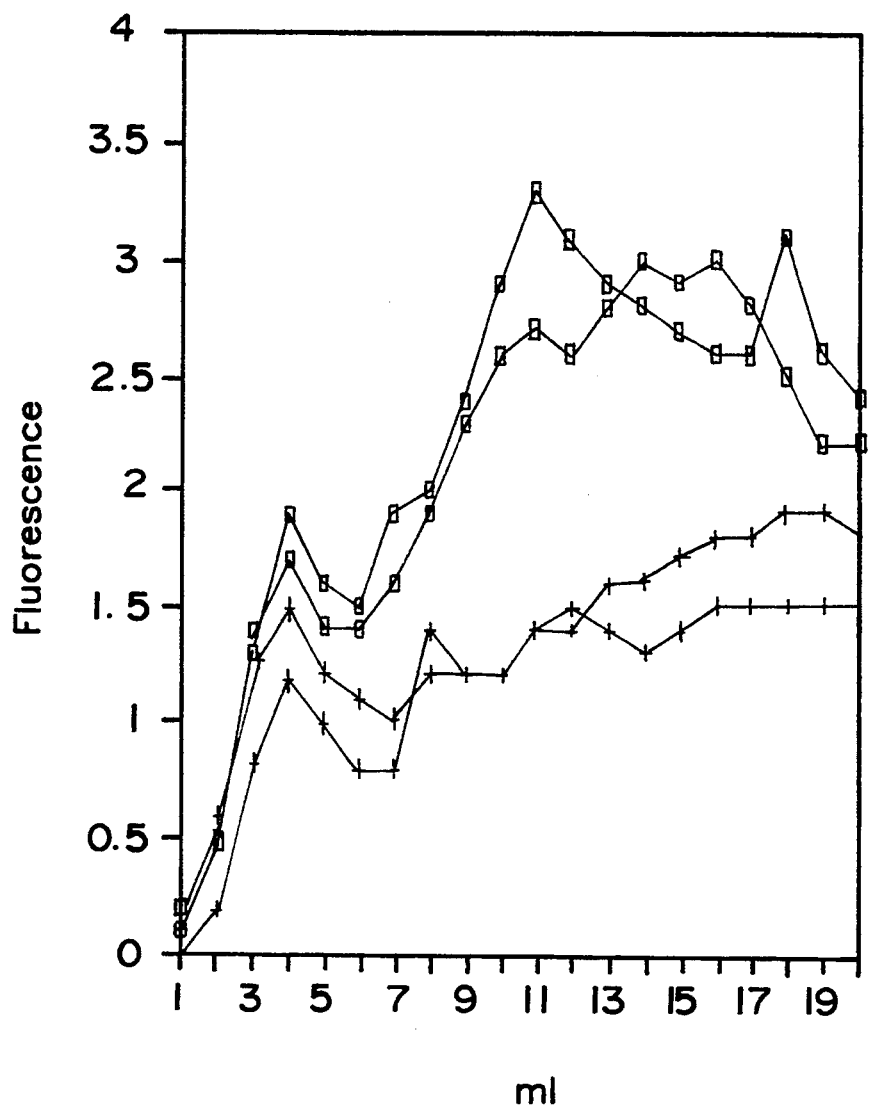
FIG. 5 shows graphically the fluorescence signals of fractions of serum samples admixed with FITC-labelled anti-transferrin monoclonal antibodies, obtained from ion exchange chromatography (□ represents serum from an alcohol abuser, + serum from a non-drinker)

Procedure:
A 10 µl serum sample was mixed with ferric citrate solution in 20 times molar excess to the transferrin content of the sample, followed by addition of monoclonal mouse antihuman transferrin antibodies, being reactive to all variants of human transferrin and having been modified and labelled with fluorescein and purified to having a very homogeneous mobility in the said ion exchange system — in a 1:1 molar concentration of the serum concentration of transferrin, and in the said eluent buffer. Subsequent to a short incubation at room temperature (5–10 minutes), the mixture was eluted through the column, followed by further elution with eluent buffer. 1.0 ml fractions were collected and the fluorescence of the fractions was measured (Excitation 485 nm, Emmission 520 nm, measured on a Shimadzu spectrophotometer RF-540). FIG. 5 displays a typical pattern obtained with sera from alcoholics and non-drinkers. For comparison, a corresponding pattern obtained with samples of solution purified disialo- and tetrasialo transferrins instead of serum is shown in FIG. 6.

EXAMPLE 3

Analysis of the antibody fraction used in Example 2

FIG. 7 is a chromatogram displaying the results from preparative anion exchange chromatography of a labelled non-purified preparation of monoclonal antibodies from Example 2. From this chromatography fractions each of 0.5 ml were collected, and FIG. 8 is a chromatogram illustrating how each fraction has a very narrow or homogeneous mobility in the anion exchange chromatography systems. Chromatography was performed on a Pharmacia Mono Q HR5 anion exchange column, equilibrated with 20 mM Tris buffer, pH 8.0 (Buffer A) and eluted using an elution gradient with Buffer B (Buffer A containing 0.7M NaCl).

EXAMPLE 4

Preparation of fluorescein-labelled monoclonal Fabfragments having a substantially uniform mobility on an anion exchange matrix From commercially available ascites produced in mice by established technology using an anti-transferrin IgG-producing hybridoma, monoclonal antibodies were purified by means of ion-exchange chromatography and subsequent size exclusion gel chromatography in a phosphate buffer. The buffer is then changed to a carbonate buffer before digesting the IgG antibodies to Fab antibody fragments by the use of papain in combination with dithiothreitol.

After this enzymatic modification free thiol groups (including free thiol groups on the antibody) are blocked with iodo-acetamide which also stops the enzymatic activity. The formed Fab fragments are purified by a combination of dialysis and anionic exchange chromatography.

Purified antibody fragments (Fab) are dialyzed against a carbonate buffer pH 9.5 before modification with fluorescein-isothiocyanate. Fluorescein binds to amino-groups on the antibody and fluorescein-labelled Fab is purified by size exclusion chromatography before finally isolating a fraction of labelled Fab from an anionic exchange chromatography column. This fraction is characterized by having a high degree of homogeneity regarding the isoelectric point, thus having substantially uniform mobility on an anionic exchange matrix.

The immunoaffinity of the labelled Fab is tested by a micro-titre ELISA system using immobilized human transferrin and peroxidase-conjugated polyclonal antimouse-IgG antibodies in solution.

EXAMPLE 5

Preparation of AMCA-labelled monoclonal Fab-fragments having a substantially uniform mobility on an Anion exchange matrix From commercially available ascites produced in mice by established technology using an anti-transferrin IgG-producing hybridoma, monoclonal antibodies were purified by means of ion-exchange chromatography and subsequent size exclusion gel chromatography in a phosphate buffer. The buffer is then changed to a carbonate buffer before digesting the IgG antibodies to Fab antibody fragments by the use of papain in combination with dithiothreitol.

After this enzymatic modification free thiol groups (including free thiol groups on the antibody) are blocked with iodo-acetamide which also stops the enzymatic activity. The formed Fab fragments are purified by a combination of dialysis and anionic exchange chromatography.

Purified antibody fragments are dialyzed against a borate buffer pH 8.0 before the addition of 7-amino-4-methyl-coumarin-3-acetic-acid-N-hydroxy-succinimide (AMCA-NHS). AMCA-NHS is added from a DMSO solution and reacts with the free aminogroups of the Fab molecule. AMCA-Fab is purified by molecular size exclusion. chromatography and finally by an anionic exchange chromatography in order to achieve a fraction with a substantially uniform mobility in an anionic exchange matrix.

The immunoaffinity of the labelled Fab is tested by a micro-titre ELISA system using immobilized human transferrin and peroxidase-conjugated polyclonal antimouse-IgG antibodies in solution.

EXAMPLE 6

Preparation of RESO-labelled monoclonal fab-fragments having a substantially uniform mobility in an anion exchange matrix From commercially available ascites produced in mice by established technology using an anti-transferring IgG-producing hybridoma, monoclonal antibodies were purified by means of ion-exchange chromatography and subsequent size exclusion gel chromatography in a phosphate buffer. The buffer is then changed to a carbonate buffer before digesting the IgG antibodies to Fab antibody fragments by the use of papain in combination with dithiothreitol.

After this enzymatic modification free thiol groups (including free thiol groups on the antibody) are blocked with iodo-acetamide which also stops the enzymatic activity. The formed Fab fragments are purified by a combination of dialysis and anionic exchange chromatography.

Purified antibody fragment are dialyzed against a 0.1 M carbonate buffer pH 8.5. N-(Resorufin-4-carbonyl)-piperidine-4-carboxylic-acid-N'-hydroxysuccinimide ester (RESOS) in a DMSO solution is added in molar excess and reacts with the amino-groups of the antibody under room temperature incubation. Labelled Fab is purified by a molecular size exclusion column followed by anionic exchange chromatography. A fraction with substantially uniform mobility on the anionic exchange matrix is isolated.

The immunoaffinity of the labelled Fab is tested by a micro-titre ELISA system using immobilized human transferrin and peroxidase-conjugated polyclonal antimouse-IgG antibodies in solution.

EXAMPLE 7

Assessment of desialylated transferrins in sera from patients

The test for desialylated transferrin is performed on iron-saturated serum samples. Iron saturation is performed by adding 5 $\mu$l FeCl$_3$, 0.25 mg/ml, in a 0.2 M Tris-Maleate pH 7.0 solution to 20 $\mu$l serum and incubation at room temperature for 20 min.

The test solution consist of 10.2 $\mu$l iron-saturated serum added to 500 $\mu$l 20 mM Tris-HCl, 70 mM NaCl, 0.05% Tween-20, pH 8.0 containing $5*10^{-8}$ M FITC-Fab (fluorescein-labelled anti-transferrin-Fab, according to Example 4 above). This solution is incubated for 15 min at room temperature before separation on a strong anionic exchange column. 500 $\mu$l of the FITC-Fab-transferrin-complex-containing solution is separated by elution with 20 mM TRIS-HCl, 70 mM NaCl, 0.05% Tween, pH 8.0 on a MonoQ (Pharmacia) column. FIG. 9 Shows the results of elution of FITC-Fab-transferrin complexes from serum samples from a heavy drinker and a normal subject. The fluorescence in fraction 1 represents unbound Fab, the fluorescence in fractions 3–7 represents FITC-Fab bound to desialylated transferrin and fluorescence in fractions greater than 9 represents FITC-Fab bound to normal transferrin. Differences in fluorescence in fractions lower than no. 7 discriminate between heavy alcohol consumers and individuals not abusing alcohol.

EXAMPLE 8

Assessment of desialylated transferrins in sera from patients using disposable minicolumns Disposable columns are prepared from strong anionic exchange gel (Q-Sepharose, Pharmacia) by using 0.5 ml of the gel in a column with inner diameter 0.7 cm. The column is equilibrated with 20 mM Tris-HCl, 70 mM NaCl, 0.05% Tween-20, pH 8.0.

The test on the minicolumn for desialylated transferrin is performed on iron-saturated serum samples. Iron saturation is performed by adding 5 $\mu$l FeCl$_3$ 0.25 mg/ml in a 0.2 M Tris-Maleate pH 7.0 solution to 20 $\mu$l serum and incubation at room temperature for 20 min.

The test solution consists of 10.2 $\mu$l iron-saturated serum added to 500 $\mu$l 20 mM Tris-HCl, 70 mM NaCl, 0.05% Tween-20, pH 8.0 containing $5*10^{-8}$ M FITC-Fab (fluorescein-labelled anti-transferrin-Fab, according to Example 4 above). This solution is incubated for 15 min at room temperature before separation on a strong artionic exchange column. 100 $\mu$l of the FITC- Fab-transferrin-complex-containing solution is added to the column and 3.0 ml of 20 mM Tris-HCl, 70 mM NaCl, 0.05% Tween-20, pH 8.0 is used to elute the desialylated transferrin-F/TC-Fab complexes. The total eluate is collected and the fluorescence from fluorescein is measured and compared a standard dilution of the fluorescein-labelled Fab fragments used. The results are used to discriminate between heavy alcohol consumers and individuals not abusing alcohol.

The tables contains results from several heavy alcohol consumers and normals.

TABLES

| Serum | Ethanol use | Measured fluorescence % of Total |
|---|---|---|
| A | Alcohol abusers | 10.9 |
| B | | 8.5 |
| C | | 8.4 |
| D | | 7.8 |
| E | Non-abusers | 5.2 |
| F | | 4.8 |
| G | | 4.8 |

EXAMPLE 9

A test for desialylated transferrin (CDT) in serum (1)

MATERIALS i. Solution A: 150 kBq/ml $^{125}$I-antitransferrin-Fab, 20 mM bis-TRIS, $3.7*10^{-5}$ M $Fe^{3+}$-citrate, 66 mM NaCl, 5.9 mM HCl, 3.1 mM Na-azide, 0.05% Tween 20, pH 7.0.
ii. Solution B: 20 mM bis-TRIS, 55 mM NaCl, 5.9 mM HCl, 3.1 mM Na-azide, 0.05% Tween 20, pH 7.0.
iii. Columns for separation: 0.5 ml strong anion-exchange gel (Q-Sepharose Fast Flow, Pharmacia) equilibrated with solution B.
iv. Test tubes Reagents and columns are stored at 4°-8° C. for longer periods of time.

Solutions and columns are equilibrated to room temperature before use.

PROCEDURE

1: TEST SOLUTION PREPARATION
1.1: 30 μl serum is added to 220 μl Solution A in a test tube. Only ordinary serum samples are used.
1.2: The samples are incubated for 1-10 min. at room temperature.

2: COLUMN SEPARATION
2.1: The column is emptied of surplus solution by removing first the top and thereafter the bottom stopper. The solution is allowed to elute through the column and the eluate is discarded.
2.2: A tube is placed beneath the column.
2.3: 200 μl test-solution is added. Care is taken to add the test sample directly to the top filter in the column. The sample is allowed to sink into the top filter before eluting by adding 3.0 ml Solution B. The column is eluted until elution stops.

3: MEASUREMENT
3.1: The collected solution is measured by gamma-counting.
3.2: A reference curve is established based upon reference samples containing known % percentages of CDT.
3.3: % CDT in unknown serum samples are calculated using the reference curve.

EXAMPLE 10

A test for desialylated transferrin (CDT) in serum (2)

MATERIALS i. Solution A: 0.14 mg/ml fluorescein-labelled-antitransferrin-Fab, 5 mM TRIS, 55 mM NaCl, pH 8.0, 3.1 mM sodium azide.
ii: Solution B: 20 mM bis-TRIS, $3.7*10^{-5}$ M $Fe^{3+}$-citrate, 66 mM NaCl, 5.9 mM HCl, 3.1 mM Na-azide, 0.05% Tween 20, pH 7.0.
iii: Solution C: 20 mM bis-TRIS, 66 mM NaCl, 5.9 mM HCl, 3.1 mM Na azide, 0.05 & Tween 20, pH 7.0.
iv. Solution D: 1.0 M TRIS-base, 3.1 mM Na azide.
v: Columns for separation: 0.5 ml strong anion exchange gel (Q-Sepharose Fast Flow, Pharmacia) equilibrated with solution C.
vi: Test tubes Reagents and columns are stored at 4°-8° C. for longer periods of time.

Solutions and columns are equilibrated to room temperature before use.

Solution A and solutions containing A should be protected from light.

PROCEDURE

1: DAILY PREPARATION OF INCUBATION SOLUTION
1.1: Solution B is mixed with Solution A by mixing
    1 part Solution A with
    10 parts Solution B
1.2: Incubation solution is prepared sufficient for one day's testing only. A minimum of 230 μl is needed for each test, plus 20 μl for reference measurement.

2: TEST PREPARATION
2.1: 30 μl serum is added to 220 μl Incubation solution (see above) in a test tube. Only ordinary serum samples should be used.
2.2: The samples are incubated for 1-10 minutes at room temperature.

3: COLUMN SEPARATION
3.1: The column is emptied of surplus solution by removing first the top and thereafter the bottom stopper. The solution is allowed to elute through the column and the eluate discarded.
3.2: A Cuvette is placed beneath the column.
3.3: 200 μl test-solution is added. Care is taken to add the test sample directly to the top filter in the column. The sample is allowed to sink into the top filter before eluting by adding 3.0 ml Solution C. Elution is continued until it stops.
3.4: 0.1 ml Solution D is added to the collected eluate and mixed by inverting the cuvette.

4: MEASUREMENT
4.1: The collected solution is measured by fluorescence. Excitation 485 nm (range 480–490) and emission 520 nm (range 515–525).
4.2: Sample for Zero setting:
    3.0 ml Solution C +
    0.1 ml Solution D.
4.3: The % CDT in an unknown sample can be determined from a standard curve established by measurement of standard sera.

EXAMPLE 11

Fractionation in batch format

Assay solution

300 μl 20 mM Bis-Tris with 50 mM NaCl and 0.05% Tween, pH 7.0 + 1.3 μl 50 mM tris maleate 9.25 mmol/l $Fe^{3+}$-citrate + 9 μl of a solution comprising 0.5 μg fluorescein labelled FAB fragments.

Particles

AQ quaternary amine particles from Dyno Particles, Norway.

PROCEDURE

1. To the assay solution, a 4 μl serum sample is added.
2. A particle suspension in 20 mM Bis-Tris buffer with 50 mM $NaCl_2$ and 0.05% Tween, pH 7, is added to a final volume of 40 vol. % particle suspension, and the suspension is agitated for 10 minutes, followed by centrifugation at 1500 g for 5 minutes.
3. The fluorescence of the supernate is measured.

EXAMPLE 12

Fluorescence labelling of antibody Fab-fragments 1. 2.5 mg Fab in 50 mM carbonate-buffer pH 9.5 is added to 25 μg fluorescein-isothiocyanate (FITC-)FITC is prepared from FITC on celite (10%) dissolved in dimethyl-sulphoxide.
2. The Fab and FITC solution is incubated in room temperature in the dark for 18–24 hours.
3. Fluorescein-Fab is purified by molecular size gel-chromatography (Superose 6 PrepGrade, Pharmacia, 1,30cm). The labelled Fab-fragment is eluted by a 10 mM Na-phosphate, 0.5 M NaCl, pH 7.4 buffer. The Antibody fraction is isolated.
4. The collected fluorescein-Fab solution is buffer-changed to 2.5 mM TRIS-HCl, pH 8.0 and further processed by strong anionic exchange chromatography.

The above procedure has been used to label Fab fragments obtained from monoclonal antibodies reactive against all variants of transferrin. Anti-transferrin antibodies (IgG) were purified from commercially available ascites, the IgG molecules were digested using papain and the free thiol groups thereby formed were blocked using iodoacetamide following conventional procedures. The resulting Fab fragments were purified by anion exchange chromatography and were then subjected to the labelling procedure set out above.

EXAMPLE 13

Iodine-$^{125}$I-labelling of antibody Fab-fragments 1. 5 mCi $^{125}$I-Bolton Hunter reagent dissolved in benzene is evaporated to dryness by the use of nitrogen-gas.
2. 0.65 mg Fab dissolved in 0.1 M borate solution pH 8.5, volume 0.96 ml is added to the $^{125}$I-Bolton-Hunter reagent and incubated/shaken on ice for 30 min.
3. 50 mM glycine in 0.1 M borate, pH 8.5, 0.5 ml is added to stop the reaction. The solution is further incubated on ice for 10 min.
4. The reaction solution is then chromatographed on a size exclusion column (Superose 6 PrepGrade, Pharmacia, 1×30cm). The labelled Fab-fragment is eluted by a 10 mM Na-phosphate, 0.1 M NaCl, pH 7.4 buffer. The antibody fraction is isolated.
5. Isolated $^{125}$I-Fab is buffer changed to 2.5 mM TRIS-HCl, pH 8.0 by ultracentrifugation with molecular cut-off 10,000 and concentrated to 1.5 ml.
6. Further processing is by strong ion-exchange chromatography.

Anti-transferrin Fab fragments, obtained as described in Example 12 were labelled using the above procedure.

I claim:

1. A method of assessment of the concentration of a subset of variants in a population of proteinaceous analyte variants capable of separation by a fractionation system, wherein said population of variants is contacted with a population of labelled proteinaceous specific binding partners therefor to form labelled binding partner-analyte complexes therewith, which are then subjected to separation by the said fractionation system into one or more fractions containing said subset of analyte variants in complexed form and assessment of the amount of label in one or more fractions so obtained, the said population of specific binding partners having, prior to reaction, substantially uniform distribution or mobility in said fractionation system, wherein said fractionation system is not SDS-PAGE.

2. A method as claimed in claim 1 wherein the specific binding partner for the analyte variant is an antibody or a fragment thereof.

3. A method as claimed in claim 1 wherein the specific binding partner is monovalent.

4. A method as claimed in claim 3 wherein the specific binding partner is a F(ab) fragment of an antibody.

5. A method as claimed in claim 1 wherein the fractionation system is based on charge or isoelectric point.

6. A method as claimed in claim 1 for the assessment of variants of transferrin.

7. A method as claimed in claim 6 wherein the fractionation system is selected from ion exchange, chromatofocusing or isoelectric focusing.

8. A method as claimed in claim 6 additionally comprising saturating the population of transferrin variants with ferric ions prior to or simultaneously with the separation step.

9. A method as claimed in claim 1 wherein substantially uniform distribution or mobility of the specific binding partner population in said fractionation system is obtained by modification and/or fractionation.

10. A method as claimed in claim 1 wherein the proteinaceous analyte variants share a common biological function or property which is antigenicity or enzymatic activity.

11. A method as claimed in claim 10, wherein the common biological function is common antigenicity.

12. A method as claimed in claim 1, wherein the proteinaceous analyte variants are glycoprotein variants differing in the extent of glycosylation.

13. A method as claimed in claim 1 for assessment of variants of transferrin, wherein the specific binding partner is monovalent and is an antibody or a fragment thereof and the fractionation system is based on charge or isoelectric point.

14. A method as claimed in claim 1 wherein the population of analyte variants is present in excess of the binding partner population, whereby an assessment of the relative amounts of one or more different variants relative to the total concentration of all variants, is obtained.

15. A method as described in claim 7 wherein the population of analyte variants is present in excess of the binding partner population, whereby an assessment of the relative amounts of one or more different variants relative to the total concentration of all variants, is obtained.

* * * * *